United States Patent [19]

Cipullo et al.

[11] Patent Number: 5,399,789
[45] Date of Patent: Mar. 21, 1995

[54] PROCESS AND COMPOSITION

[75] Inventors: Michael J. Cipullo; John W. Fulmer, both of Mt. Vernon, Ind.

[73] Assignee: General Electric Company, Pittsfield, Mass.

[21] Appl. No.: 245,338

[22] Filed: May 18, 1994

Related U.S. Application Data

[60] Division of Ser. No. 10,898, Jan. 29, 1993, Pat. No. 5,336,813, which is a continuation of Ser. No. 611,562, Nov. 13, 1990, abandoned.

[51] Int. Cl.$^6$ ............... C07C 37/68; C07C 39/16; C07C 37/88; C07C 37/20
[52] U.S. Cl. ................. 568/702; 568/701; 568/722; 568/724; 252/182.24; 252/182.29
[58] Field of Search ......... 568/701, 722, 724, 702, 568/716; 252/182.24, 182.29

[56] References Cited

U.S. PATENT DOCUMENTS

| 3,438,908 | 4/1969 | Reymore et al. | 272/182 |
|---|---|---|---|
| 4,191,843 | 3/1980 | Kwantes et al. | 568/727 |
| 4,240,968 | 12/1980 | Quinn et al. | 568/724 |
| 4,423,252 | 12/1983 | Maki et al. | 568/728 |
| 4,535,191 | 8/1985 | Mark et al. | 568/728 |
| 4,766,254 | 8/1988 | Faler et al. | 568/724 |
| 4,847,433 | 7/1989 | Kissinger | 568/727 |
| 4,894,486 | 1/1990 | Neil, Jr. et al. | 568/702 |
| 4,918,245 | 4/1990 | Iimuro et al. | 568/727 |
| 5,008,470 | 4/1991 | Powell et al. | 568/727 |
| 5,098,603 | 3/1992 | Perlman | 252/182.29 |
| 5,124,490 | 6/1992 | Cipullo | 568/724 |
| 5,336,813 | 8/1994 | Cipullo et al. | 568/724 |

FOREIGN PATENT DOCUMENTS

| 329075 | 8/1989 | European Pat. Off. |
| 6112639 | 6/1984 | Japan |
| 6112640 | 6/1984 | Japan |
| 890432 | 6/1960 | United Kingdom |

*Primary Examiner*—Werren B. Lone

[57] ABSTRACT

A process comprising the addition of a degradation inhibiting effective amount of an amine having a boiling point above that of the phenol used in the process to a composition comprising the said phenol and a bisphenol, the addition occurring prior to a procedure which subjects the bisphenol to substantial heat, said bisphenol produced from an acidic ion exchange resin catalyzed reaction of the said phenol and a ketone or aldehyde.

5 Claims, No Drawings

PROCESS AND COMPOSITION

This is a divisional of application Ser. No. 08/010,898, filed on Jan. 29, 1993, U.S. Pat. No. 5,336,813, which is a continuation of Ser. No. 07/611,562, filed Nov. 13, 1990, now abandoned.

BACKGROUND OF THE INVENTION

The dihydric phenols have achieved significant success in their commercial applications. Dihydric phenols are useful in the commercial manufacture of various polymers including the polyarylates, polyamides, epoxies, polyetherimides, polysulfones and the polycarbonates. Significant attention has been directed to the commercial preparations of the dihydric phenols. For many years it has been well known that the acid catalyzed reaction of phenol with specific aldehyde or ketone could prepare the 4,4'-dihydric phenol with specific groups derived from the aldehyde or the ketone connecting the two phenolic rings. In particular when phenol is reacted with acetone, the dihydric phenol 4,4'(hydroxyphenyl)propane-2, hereafter known as bisphenol-A is formed. This has particular utility in polycarbonates, polyarylates and copolyestercarbonates as well as epoxies. In order to make certain polymers, in particular the polycarbonates, the bisphenol-A must be particularly pure, for example, as measured by color. Additionally, the process should be particularly efficient since the dihydric phenol costs contribute substantially to the cost of the final polymer. Therefore much attention has been directed to the recovery of bisphenol-A after preparation. Not only is recovery from the major stream containing primarily bisphenol-A important, but because of the economics involved, various side streams or "purge streams" also contain significant quantities of bisphenol-A and should also be processed in manners which maximize bisphenol-A recovery.

Various catalytic systems for acid catalysis of the reaction between phenol and acetone have been investigated and used commercially. At one time the hydrochloric acid catalyzed process was used in a significant number of commercial facilities. However the corrosion caused by the hydrochloric acid on standard metallic reactors and pre and post reaction equipment left much to be desired as far as replacement economics was concerned. Recently, substantial attention has been placed on using an ion exchange resin catalyst system since it does not have significant acid corrosion problems.

Various tactics have been utilized to maintain the quality and quantity of bisphenol-A which has been recovered from the acidic ion exchange resin catalyzed reaction of phenol and acetone. U.S. Pat. No. 4,847,433 utilizes a carbonate system, specifically the alkaline earth and transition metal oxidation number plus two salts of carbonates, to stabilize the bisphenol-A so that significant quantities of quality bisphenol-A can be recovered from various streams. It was thought that the specific acidic material that was being counteracted by the addition of the carbonate salts were minute quantities of strong acid oligomers which were being leached from the resin catalyst during the processing. It was noted that such carbonate salts should not be recycled to the catalyst system since they would very well bring about eventual neutralization of the catalyst system.

U.S. Pat. No. 4,894,486 specifically states that the presence of metal ions is also thought to have an adverse effect on the color of bisphenols probably by promoting degradation. The British Patent 890432 is then cited to show that various other additives have been employed to inhibit the formation of degradation products of the bisphenols. Thus, alkaline earth phosphates, stannic oxide and oxylate, a mixture of tin powder and tin dioxide, terephthalic and isophthalic acids, oxalic, sebacic and adipic acids and boron or antimony trioxides and their mixtures are taught as useful additives for providing thermal stabilities to bisphenols. Additionally in British Patent 890432 is mentioned the concept of utilizing a neutral or amphoteric compound or compound of weakly acidic character and possibly also possessing the property of forming complexes with metallic ions and ability to react with alkaline reacting impurities in the bisphenols is also mentioned. A further British Patent 1022583 teaches that improved color stability of bisphenols is provided by the incorporation of oxalic, citric or tartaric acids or their alkali metal or ammonium salts during a bisphenol manufacturing process. They may be added with the reactants or after the reaction is complete but before the bisphenol is separated from the reaction mixture. The British patents disclose acidic conditions for preparing bisphenol-A but no mention of acid ion exchange resin catalysis is mentioned.

Recently, U.S. Pat. No. 4,894,486 disclosed the use of the hydroxy acids lactic, malic and glyceric and their ammonium or alkali metal salts as stabilizers for bisphenols. No particular preparation of the bisphenol-A was employed and the only examples utilized the acid per se and measured the APHA color before and after heat treatment.

Weakly basic anion exchange columns have also been utilized to contact bisphenol containing fluids. In U.S. Pat. No. 4,191,843, a weakly basic anion exchange resin is used to contact reactor effluent obtained from an acid ion exchange resin catalyst. Instead of the weakly basic anion exchange resin, strongly acidic ion exchange resin in its salt form can also be used. U.S. Pat. No. 4,766,254, utilizes a weakly basic anion exchange resin to contact the mother liquor of bisphenol-A phenol adduct. Additionally salts of nitric, sulfuric and phosphoric acid ($NaH_2PO_4$) have been used as bisphenol stabilizers, see Japan 61 12639 and Japan 61 12640. A recent European patent application, EPA 329 075 discloses the use of a polyvinyl pyridine anion exchange column to stabilize bisphenols.

As can be seen from this virtual potpourri of prior art there is very little distinction given to the types of impurities which are being addressed in the manufacturing process of bisphenols, particularly bisphenol-A. The fact that any of acids, salts of acids, certain bases or basic ion exchange resins can be used indicates that both alkaline and acidic impurities are being removed. Therefore there is no real directing nature to the prior art.

It is now been found that when utilizing an acidic ion exchange resin to catalyze a reaction between a phenol and a ketone to produce a bisphenol, particularly phenol and acetone to produce bisphenol-A, it is very advantageous to contact the desired bisphenol produced prior to significantly elevated temperatures such as distillation to separate bisphenol-A from various impurities including phenol as well as the separation of bisphenol-A from bisphenol-A phenol adduct, with certain amines. These amines are selected so they have a boiling point above that of the phenol used in the process. In this manner significant stabilization of the bisphenol, particularly bisphenol-A, is achieved when the bisphenol is subjected to a heat treatment, for example distillation of phenol or the bisphenol or separation from its adduct of bisphenol with phenol. Degradation is significantly inhibited as shown by the substantial quantity of bisphenol which is capable of recovery. Additionally reduced color of the bisphenol is often observed when salts of the acid of this invention are in contact therewith.

SUMMARY OF THE INVENTION

In accordance with the invention, there is a process comprising the addition of a degradation inhibiting effective amount of an amine having a boiling point above that of the phenol used in the process, to a composition comprising a phenol and a bisphenol the addition occurring prior to a procedure which subjects the bisphenol to substantial heat, said bisphenol produced from an acid ion exchange catalyzed reaction of a phenol and a ketone or aldehyde.

A further aspect of the invention is a composition comprising phenol and a bisphenol in admixture with a bisphenol degradation inhibiting effective amount of an amine having a boiling point above that of the phenol.

DETAILED DESCRIPTION OF THE INVENTION

The bisphenol, particularly bisphenol-A, is made by the standard acid catalyzed reaction of a phenol and an aldehyde or ketone. When preparing bisphenol-A, the phenol is phenol and the ketone is acetone. An acidic catalyst is used to increase the efficiency of the reaction. This catalyst system is preferably in the heterogeneous form, that is as an ion exchange resin in its acidic form. The problems using a homogeneous catalyst system such as hydrochloric acid are well known and should be avoided. The ion exchange resin can be for example an Amberlite type resin obtained from Rohm and Haas. This resin has styrenic backbone with pendant $SO_3H$ groups which provide the acidic character to the resin. Usually the styrene is crosslinked with a small quantity of divinyl benzene or other crosslinking chemical. This addition of a crosslinker appears to provide structural strength and rigidity to the catalyst. Other ion exchange resins can also be used although it is preferable to use the styrenic backbone crosslinked with the difunctional monomer and having $SO_3H$ groups pendant from the aromatic nucleus of the styrene moiety. The use of these ion exchange resins can bring about certain problems not previously observed with a homogeneous acidic catalyst system. Increased color of the bisphenol-A as well as loss of bisphenol-A during certain heat treatments such as distillation and/or bisphenol-A phenol adduct melting and separation were found to occur.

The group of compounds which inhibit the degradation of the bisphenol is an amine having a boiling point higher than the phenol used in the process. By having the higher boiling point than the phenol, the unreacted amines are present but are not passed back with recycle phenol to the original condensation catalyst wherein neutralization of that acidic catalyst system could rapidly occur. Such unreacted amine and any salt formed during a neutralization is rather passed along with the bisphenol product stream and surprisingly does not seem to cause any undesirable effects. In fact wherein the bisphenol is used in further processing involving the preparation of polymer using an amine catalyst system, for example the interfacial polymerization of aromatic polycarbonate from bisphenol and carbonate precursor, amine is common to the system and is removed at an appropriate point.

Usage of such amines have advantages over other materials used, particularly the carbonates, specifically barium carbonate. Generally the amine has improved solubility in phenolic solutions and water compared to metal carbonates. This provides more efficient use of the additive and the option to easily add the material as a liquid solution rather than a solid powder. Additionally there is no major toxicity problem associated with the amine as there is with the metallic carbonates, particularly barium carbonate.

These salts can be added to the process of preparing the bisphenol prior to any substantial heat treatment for maximum effect. Examples of such heat treatment include distillation, melting the adduct of bisphenol and phenol and like elevated temperature treatments.

As stated previously, the amines should have a boiling point which is significantly higher than the phenol being used. This allows for a substantial separation of the phenol and amine upon distillation of the phenol and allows for the amine to be separated with the bisphenol. When utilizing phenol per se, B.P. 182° C. the following amines are examples of those amines which are effective in the process.

| Amine | B.P. °C. |
|---|---|
| p-phenylene diamine | 267 |
| N,N-diethylaniline | 217 |
| tributylamine | 216 |
| N,N-dimethylaniline | 193 |
| hexamethylene diamine | 200 |
| tridodecylamine | 220–228 @ 0.03 mm Hg |
| dioctylamine | 298 |
| diphenylamine | 302 |
| 4-dodecylaniline | 220 @ 15 mm Hg |
| trioctylamine | 365 |
| 4-methylbenzylamine | 195 |

The amines are preferably either liquid at the process stream temperature or at least substantially soluble in the process stream.

A stabilizing effective or degradation effective amount of the compound(s) should be employed. Generally an effective amount of from about 1 to about 1000 ppm based upon the bisphenol present in the stream is efficient. Below this quantity, effectiveness is difficult to observe. Above this quantity, no additional beneficial results are generally observed. Preferred quantities are generally from about 10 to about 500 ppm can also be employed as well.

Below are examples of the invention. These examples are intended to illustrate and exemplify but not narrow the invention.

EXAMPLES

Bisphenol-A is prepared from the strong acid ion exchange resin catalyzed reaction of acetone and phenol. Lewatit, ion exchange resin from Mobay is used. This is a sulfonic acid substituted cross linked polystyrene. The bisphenol-A is separated as bisphenol-A phenol adduct. Approximately 250 grams of mother liquor of bisphenol-A phenol adduct was placed in a 500 ml pot. The quantity of bisphenol-A present in the mother liquor was analyzed by high pressure liquid chromotography.

The pot is heated with the reflux condenser off and the phenol is collected over head until the pot temperature Irises to 210° C. At that point, the reflux condenser water flow is initiated and the solution is allowed to reflux for four hours. A nitrogen blanket was not used to allow air/oxygen contact during the test.

At the end of four hours, the pot residue is again analyzed by high pressure liquid chromatography to determine the weight of bisphenol-A remaining. This is the control.

The same procedure is carried out as above; however 500 ppm of additive based upon the weight of solution was added to the pot together with the mother liquor. The final quantity of bisphenol-A was reported after four hours of refluxing. Below are the results reported as percent loss of BPA from the initial quantity. 0% loss is total inhibition of degradation.

| Additive | % Loss Control | % Loss Experimental |
| --- | --- | --- |
| 1-adamantamine | 36.3 | 0 |
| N,N-dimethylaniline | 15.4 | 0 |
| Tributylamine | 16.6 | 0 |

What is claimed is:

1. A composition comprising phenol and bisphenol in admixture with a bisphenol degradation inhibiting effective amount of an amine having a boiling point above that of the phenol.

2. The composition in accordance with claim 1 wherein the bisphenol is bisphenol-A and phenol is phenol.

3. The composition in accordance with claim 2 wherein the amine is of such a boiling point that substantial separation between the amine and phenol will occur during distillation.

4. The composition in accordance with claim 2 wherein the amine is present in from about 1 to about 1000 ppm, as measured by bisphenol-A.

5. The composition in accordance with claim 4 wherein the amine is tributylamine or N,N-dimethylaniline.

* * * * *

UNITED STATES PATENT AND TRADEMARK OFFICE
CERTIFICATE OF CORRECTION

PATENT NO. : 5,399,789
DATED : March 21, 1995
INVENTOR(S) : Lyndon W. Drewlow, et. al.

It is certified that error appears in the above-indentified patent and that said Letters Patent is hereby corrected as shown below:

Title page, between "[22] filed Jul. 10, 1992" and "[51] Int. Cl.$^6$" the following:  --[*] Notice:  The portion of the term of this patent subsequent to September 13, 2011, has been disclaimed--.

Signed and Sealed this

Eighth Day of April, 1997

Attest:

BRUCE LEHMAN

*Attesting Officer*                *Commissioner of Patents and Trademarks*